Figure 1:
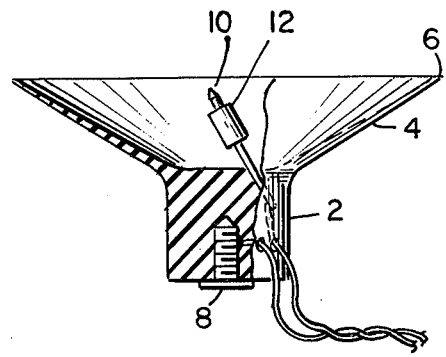

United States Patent [19]

Zilianti

[11] 4,299,232
[45] Nov. 10, 1981

[54] BIPOLAR ELECTRODES FOR FETAL HEART-RATE RECORDING DURING LABOR

[76] Inventor: Mario Zilianti, Apartado del Este 62320, Caracas, Venezuela

[21] Appl. No.: 50,016

[22] Filed: Jun. 19, 1979

[51] Int. Cl.³ .............................................. A61B 5/04
[52] U.S. Cl. .................................... 128/642; 128/643
[58] Field of Search ............... 128/642, 643, 784, 785, 128/788, 802, 635

[56] References Cited

U.S. PATENT DOCUMENTS

| 2,660,175 | 11/1953 | Thrasher et al. | 128/643 |
| 3,505,993 | 4/1970 | Lewes et al. | 128/643 |
| 3,534,733 | 10/1970 | Phipps et al. | 128/643 |
| 4,157,710 | 6/1979 | Abitol | 128/642 |

FOREIGN PATENT DOCUMENTS

| 2152808 | 4/1973 | Fed. Rep. of Germany | 128/643 |
| 1535432 | 8/1968 | France | 128/643 |
| 1260919 | 1/1972 | United Kingdom | 128/642 |
| 162281 | 10/1962 | U.S.S.R. | 128/642 |

OTHER PUBLICATIONS

Rosen et al., "The Human Fetal Electroencephalogram", Am. J. Ob. & Gyn., vol. 104, pp. 1057–1060, 1969.

Primary Examiner—Lee S. Cohen
Attorney, Agent, or Firm—Ladas & Parry

[57] ABSTRACT

A bipolar electrode for fetal heart-rate recording comprises a flexible cup having a base portion and a substantially frusto-conical portion secured to and flaring outwardly from the base portion and defining a rim of the cup. The electrode further comprises a first electrode pole which is pointed and is of rod form and extends into the interior of the cup from the base portion. A second electrode pole is exposed to the exterior of the cup. The cup is applied to the fetal scalp and upon pressing the rim of the cup into contact with the fetal scalp the point of the first electrode pole pierces the fetal skin and the cup becomes adhered by suction to the fetal scalp while the second electrode pole makes electrical contact with maternal liquid.

6 Claims, 5 Drawing Figures

BIPOLAR ELECTRODES FOR FETAL HEART-RATE RECORDING DURING LABOR

This invention relates to bipolar electrodes for fetal heart-rate (FHR) recording during labor.

According to the present invention there is provided a bipolar electrode for fetal heart-rate recording, comprising a flexible cup having a base portion and a substantially frusto-conical portion secured to and flaring outwardly from the base portion and defining a rim of the cup, and the electrode further comprising a first electrode pole which is pointed and is of rod form and extends into the interior of the cup from said base portion, and a second electrode pole which is exposed to the exterior of the cup, whereby the cup may be applied to the fetal scalp and upon pressing the rim of the cup into contact with the fetal scalp the point of the first electrode pole pierces the fetal skin and the cup becomes adhered by suction to the fetal scalp while the second electrode pole makes electrical contact with maternal liquid.

Figure 2:
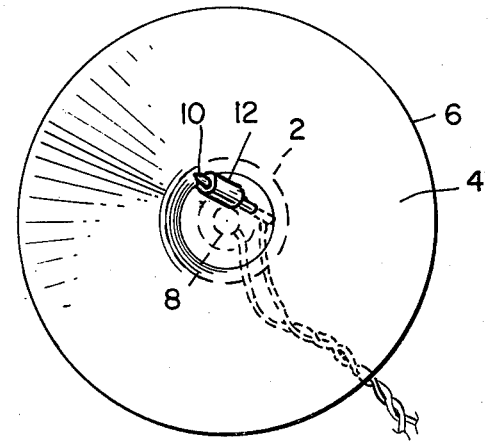
Figure 3A:
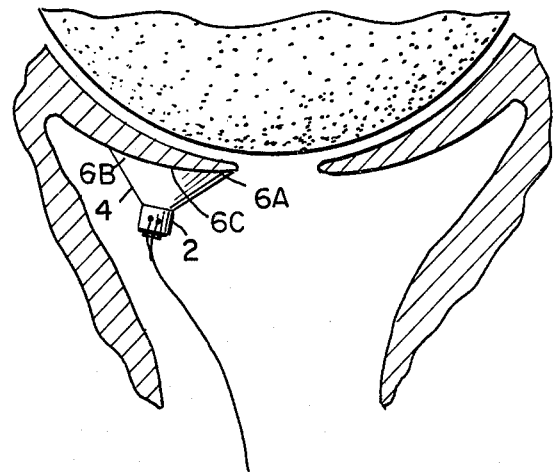
Figure 3B:
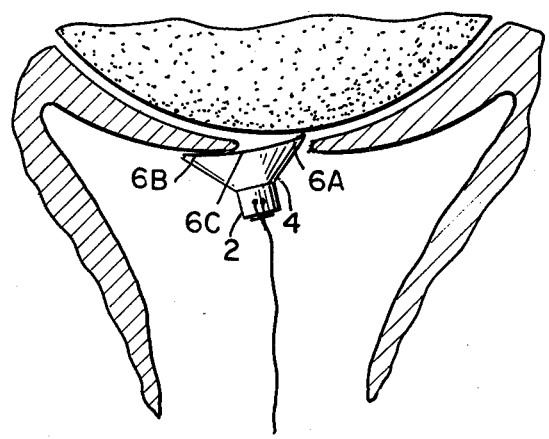
Figure 3C:
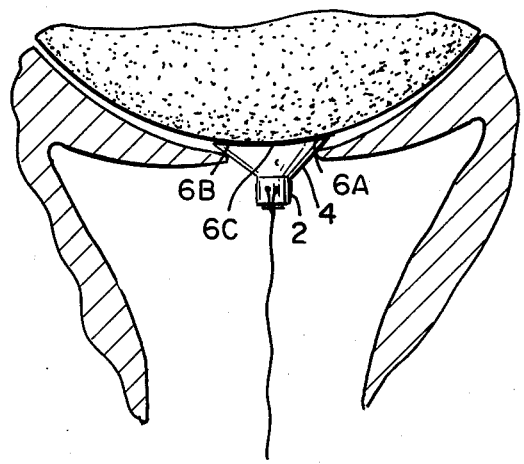

For a better understanding of the invention, and to show how the same may be carried into effect, reference will now be made, by way of example, to the accompanying drawings in which:

FIG. 1 shows a part cross-sectional view of a bipolar electrode for FHR recording, FIG. 2 illustrates a plan view of the electrode, FIGS. 3(a), 3(b) and 3(c) illustrate application of the electrode to the fetal scalp.

The illustrated electrode comprises a flexible cup which has a cylindrical base 2 and a generally frusto-conical wall 4 secured to the base and flaring outwardly therefrom to a circular rim 6. The base 2 has a diameter of approximately 1.4 cm, and the maximum diameter of the wall 4 is approximately 3.5 cm. A small metal screw 8 is fitted in a central hole in the base 2, the head of the screw being exposed at the underside of the base and being smoothed to remove rough edges. The screw does not extend quite through the base 2, but stops short of the upper edge thereof.

A metallic rod 10 is embedded in the base 2 and projects upwardly from the upper surface thereof into the interior space defined by the cup. The rod is pointed at its upper end, which is just below the plane in which the rim 6 is located, and extends obliquely with respect to that plane. On the rod is carried a cylinder 12 of synthetic plastic material. This cylinder is shorter in length than the length of the rod protruding from the base, and is slidable along the rod, so that when the cylinder is pressed downwardly along the rod the point at the upper end of the rod is exposed.

Two insulated electrical conductors extend into the interior of the base 2 through the lateral wall thereof, and establish electrical connection within the base to the screw 8 and the lower end of the rod 10. The passages through which the conductors enter the base are sealed in fluid tight manner.

The electrode is applied when the fetal head is engaged and the cervix is dilated at least 3 cm. The cup is placed in position with the rim 6 of the cup touching the cervix, as shown in FIG. 3(a). The cup adheres to the cervix without it being necessary to apply pressure, in much the same manner as two glass microscope slides adhere together when there is a film of liquid therebetween. The physician is then able to slide the electrode over the cervix without its becoming detached from the cervix, and because the point of the rod is below the plane in which the rim 6 is located the point of the rod does not pierce the cervix, and therefore the sliding of the electrode over the cervix does not damage the cervix. The physician slides the electrode over the cervix to cause one edge 6A of the cup to enter the cervical opening and come into contact with the fetal scalp, as shown in FIG. 3(b). The electrode is then moved further over, passing the edge 6A of the cup between the fetal scalp and the inner surface of the cervix until the opposite edge 6B of the cup is able to enter the cervical opening and come into contact with the fetal scalp. It will be appreciated that during this movement of the cup through the cervical opening the wall 4 of the cup must be bent somewhat, to bring the edge 6C and the opposite edge close enough together to pass through the cervical opening. When the entire rim of the cup has passed through the cervical opening and is in contact with the fetal scalp, the electrode adheres to the fetal scalp in the same way as it previously adhered to cervix. The electrode is then slid back somewhat, to the position shown in FIG. 3(c) in which it is centered with respect to the cervical opening. When the electrode is in the desired position, pressure is applied to the base of the cup in order to expel fluid from the cup, so that it will be held firmly in position by suction, and to cause the point to pierce the fetal skin. The oblique orientation of the rod provides for increased contact area with the rod and also causes the rod to "hook" onto the fetal skin and thereby resists any tendency for the point to become detached.

The cylinder 12 carried on the rod protects the maternal parts and the fingers of the physician from the point during application of the electrode, but when pressure is applied to the base of the cup the cylinder is displaced along the rod and exposes the point and permits it to penetrate the fetal skin. The cylinder also imposes a limit upon the penetration of the rod into the fetal scalp, in that the cylinder cannot be pressed along the rod beyond the point at which the rod projects from the upper surface of the base 2.

When the electrode is in position, with the rod 10 piercing the fetal scalp and the screw 8 in contact with maternal liquid, the terminals of the conductors are connected to a recording machine.

The illustrated electrode is easier to apply than the known spiral electrode and is practically not aggressive, i.e. the electrode creates very little danger of serious injury to the fetus. The penetration of the needle is less than 1 mm, and since the point of penetration is isolated under the suction cup, the possibility of infections of the fetal scalp is reduced. From the maternal point of view, the application of the electrode is hardly distinguishable from a routine pelvic examination.

In order to remove the electrode when it is out of sight, a gentle but firm traction is applied to it through the electrical conductors. If this is not successful, a pelvic examination is carried out and the rim of the cup is detached carefully from the fetal scalp while maintaining traction on the conductors.

The invention is not limited to the particular electrode described and illustrated, since variations may be made in the construction of the electrode without departing from the principles of the invention as defined in the appended claims.

I claim:

1. A bipolar electrode assembly for fetal heart-rate recording, comprising a cup having a base portion and a flexible substantially frusto-conical portion secured to and flaring outwardly from the base portion and defining a rim of the cup, and the electrode assembly further comprising a first electrode which is pointed and is of rod form and extends into the interior of the cup from said base portion, a second electrode which is attached to the cup and is exposed to the exterior of the cup, and means for connecting the first and second electrodes to opposite poles of a readout instrument, whereby the cup may be applied to the fetal scalp and upon pressing the rim of the cup into contact with the fetal scalp the point of the first electrode pierces the fetal skin and the cup becomes adhered by suction to the fetal scalp while the second electrode makes electrical contact with maternal liquid.

2. An electrode assembly as claimed in claim 1, wherein the rim of the cup defines a plane, and the first electrode extends into the interior of the cup obliquely with respect to said plane.

3. An electrode assembly as claimed in claim 1, wherein the rim of the cup defines a plane, and the first electrode extends into the interior of the cup from said base portion but terminates short of said plane.

4. An electrode assembly as claimed in claim 1, 2 or 3 further comprising a hollow cylinder of synthetic plastic material fitted slidingly on said first electrode, so that when the cylinder slides along the rod towards the base portion of the cup the point of the first electrode is exposed.

5. An electrode assembly as claimed in claim 1, wherein the second electrode is fitted in said base portion.

6. An electrode assembly as claimed in claim 5, wherein both said first and said second electrodes are embedded in said base portion and the connecting means further comprises first and second electrical conductors which are electrically connected with the first and second electrodes respectively within said base portion.

* * * * *